US011457931B1

(12) United States Patent
Patterson et al.

(10) Patent No.: US 11,457,931 B1
(45) Date of Patent: Oct. 4, 2022

(54) BONE SHORTENING OSTEOTOMY APPARATUS

(71) Applicant: Avanti Orthopaedics LLC, Wilmington, DE (US)

(72) Inventors: John Douglas Patterson, Wilmington, DE (US); Cyrus B. Gooray, Needham, MA (US); Meredith Nita Osterman, Wayne, PA (US); Devanand Gooray, Penn Valley, PA (US)

(*) Notice: Subject to any disclaimer, the term of this patent is extended or adjusted under 35 U.S.C. 154(b) by 0 days.

(21) Appl. No.: 17/463,971

(22) Filed: Sep. 1, 2021

Related U.S. Application Data

(60) Provisional application No. 63/168,670, filed on Mar. 31, 2021.

(51) Int. Cl.
| A61B 17/15 | (2006.01) |
| A61B 17/16 | (2006.01) |
| A61B 17/80 | (2006.01) |

(52) U.S. Cl.
CPC ........ *A61B 17/151* (2013.01); *A61B 17/1697* (2013.01); *A61B 17/8019* (2013.01); *A61B 17/8095* (2013.01)

(58) Field of Classification Search
CPC .............. A61B 17/151; A61B 17/8019; A61B 17/8004; A61B 17/808
See application file for complete search history.

(56) References Cited

U.S. PATENT DOCUMENTS

| 6,007,535 A * | 12/1999 | Rayhack | ............... A61B 17/15 606/105 |
| 7,540,874 B2 | 6/2009 | Trumbel et al. | |
| 8,282,644 B2 | 10/2012 | Edwards | |
| 8,652,142 B2 | 2/2014 | Geissler | |
| 8,777,948 B2 | 7/2014 | Bernsteiner | |
| 8,939,984 B2 | 1/2015 | Budoff | |
| 9,023,052 B2 | 5/2015 | Lietz et al. | |
| 9,089,376 B2 | 7/2015 | Medoff et al. | |
| 10,390,840 B2 | 8/2019 | Verstreken et al. | |
| 10,709,458 B1 * | 7/2020 | Bini | ..................... A61B 17/154 |
| 2004/0138669 A1 | 7/2004 | Horn | |

(Continued)

FOREIGN PATENT DOCUMENTS

CN 110916791 A 3/2020

*Primary Examiner* — Amy R Sipp
(74) *Attorney, Agent, or Firm* — Invention To Patent Services; Alex Hobson

(57) ABSTRACT

A bone shortening osteotomy apparatus is configured to provide positive retention of the bone portions as the two cut bone portions are retracted. The apparatus utilizes a bone plate with a compression block detachable attached in a fixed position and a sled assembly that is slidably engaged with the bone plate. A jacking screw extends from the sled to the compression block to draw these two components together. K-wire barrels coupled to the sled converge to direct K-wires into bone. Sled guide pins extend between the sled and the compression block and preferably on opposing sides of the jacking screw to ensure straight movement of the sled toward the compression block. A cutting guide has guide slots for guiding a cutting implement through the bone. A slot wedge may be inserted through the guide slot after cutting the bone to stabilize the cutting guide and bone for subsequent cutting.

19 Claims, 8 Drawing Sheets

(56) References Cited

U.S. PATENT DOCUMENTS

| | | | |
|---|---|---|---|
| 2005/0277941 A1* | 12/2005 | Trumble | A61B 17/8004 606/79 |
| 2013/0012949 A1* | 1/2013 | Fallin | A61B 17/8886 606/87 |
| 2013/0253592 A1* | 9/2013 | Larche | A61B 17/8019 606/282 |
| 2016/0038203 A1 | 2/2016 | Huebner | |
| 2016/0310179 A1* | 10/2016 | Federspiel | A61B 17/808 |
| 2020/0008846 A1 | 1/2020 | Medoff | |
| 2020/0008847 A1 | 1/2020 | Medoff | |

\* cited by examiner

BONE SHORTENING OSTEOTOMY APPARATUS

CROSS REFERENCE TO RELATED APPLICATIONS

This application claims the benefit of U.S. provisional patent application No. 63/168,670, filed on Mar. 31, 2021; the entirety of which is hereby incorporated by reference herein.

BACKGROUND OF THE INVENTION

Field of the Invention

The invention relates to a bone shortening osteotomy apparatus for excising a portion of bone and subsequently retracting the cut portions of bone.

Background

Existing bone shortening osteotomy apparatuses often do not effectively retain the bone in alignment, especially after cutting through the bone. One or both portions of the bone may twist or become misaligned with the other portion of cut bone. The mechanisms for retracting the bone can become dislodged and are difficult to manipulate. The bone plates used do not enable securing the cut bone portions together across the excised portion of bone, or cut ends of the bone, while the retraction apparatus is still coupled with the bone.

SUMMARY OF THE INVENTION

The invention is directed to a bone shortening osteotomy apparatus for excising a portion of bone and shortening the bone by drawing the two cut ends of the bone toward each other. The bone shortening osteotomy apparatus includes a bone plate that is specifically adapted for use with the retraction portions of the bone shortening osteotomy apparatus, the compression block and sled assembly. A compression block is retained to the bone plate in a fixed position and the sled assembly is slidably engaged along the length of the bone plate. A jacking screw extends between the compression block and the sled assembly, and turning the jacking screw draws the sled assembly toward the compression block.

The cut portions of bone are stabilized and retained in alignment via the bone shortening osteotomy apparatus. A pair of K-wires extend through K-wire barrels that extend along an offset angle, or a barrel angle as used herein, to better secure the second cut portion of bone in rotational alignment with the first cut portion of bone. The barrel angle is the angle between the K-wire barrels or the apertures therethrough. The two K-wires and K-wire barrels extend non-parallel to each other and may be convergent with respect to each other toward the bone plate and bone. The distance between the openings or inlets of the K-wire barrels is greater than the distance of the outlet of the K-wire barrels, proximal to the bone, thereby directing convergent K-wires into the bone. This convergent arrangement of the K-wire barrels and the resultant convergent K-wires extending into the bone retains the sled assembly and sled down against the bone plate as the inserted ends of the K-wires in the bone produces a retaining force from the sled being lifted or tilted. The K-wire barrels may be configured on a distal end of the sled assembly from the compression block to provide additional resistance to any torque on the sled assembly from the jacking screw. The K-wire barrels may be configured on opposing sides of the bone plate wherein the convergent K-wire barrels direct the K-wires toward the center of the bone plate from an inlet opening of the K-wire barrels. The K-wire barrels may have a length from an inlet opening for receiving the K-wires to the outlet opening that is proximal to the bone plate and bone. A K-wire barrel may have a length from an inlet opening to an outlet opening of at least 4 mm or more, at least 8 mm or more, at least 12 mm or more, at least 14 mm or more, at least 20 mm or more and any range between and including the length values provided. The longer the K-wire barrel, the more support the convergent K-wires will product to retain the sled to the bone plate. The barrels may be configured at a barrel angle with respect to each other of about 10 degrees or more, about 20 degrees or more, about 30 degrees or more, about 45 degrees or more, about 60 degrees or more, about 75 degrees or more, about 90 degrees or more, about 110 degrees or more and any range, such as from about 10 degrees to about 90 degrees, between and including the barrel angles provided. A barrel angle of 90 degrees will direct the K-wires into the bone at a 45 degree angle from a normal axis, with respect to the top of the bone plate, assuming the K-wire barrels are angularly offset equally from said normal axis. A larger barrel angle will more securely retain the sled assembly to the bone plate and bone and prevent lifting of the sled assembly and bone plate from the bone, however to great of an angle may result in less purchase into the bone. A range from about 30 to 90 degrees may be preferred for these reasons.

A first cut portion of bone is retained in position with respect to the bone plate by one or more bone fasteners and in an exemplary embodiment, at least one extends through a directional aperture in the bone plate. In a preferred embodiment, bone fasteners extend through directional apertures forming an acute angle between their length axes. Directional apertures may also be convergent. The second cut portion of bone is retained to the bone plate by a bone fastener that extends through a slotted aperture, proximal to the second end of the bone plate. The slotted aperture allows the second cut portion of bone to retract toward the first cut portion of bone while retracting the bones. The second cut portion of bone is also secured in an angular position by the K-wires that extend through K-wire barrels, coupled with the sled, and into the second cut portion of bone.

A pair of sled guide pins extend between the compression block and the sled assembly to ensure that the sled moves linearly toward the compression block. In an exemplary embodiment, the sled guide pins are configured on opposing sides of the jacking screw and may extend from the sled assembly or from the compression block. It may be preferred to have the sled guide pins coupled with and extending from the sled assembly for ease of positioning the sled assembly over the bone. The sled guide pins may extend into block pin apertures in the compression block. Configuring the sled guide pins with a space between them, and particularly with them positioned on opposing sides of the jacking screw, ensures aligned movement of the sled toward the compression block. Finally, the sled assembly may be configured with channels that extend down over the sides of the bone plate, thereby further ensuring smooth and aligned motion over the bone plate.

An exemplary bone plate may have a pair of flanges that extend out from the sides of the bone plate to secure the sled and/or compression block to the bone plate, via a channel extension in these components. For example, a sled flange may be configured along a portion of the bone plate that the sled will move during retraction of the cut bone. The sled flanges may not extend the entire length of the bone plate thereby enabling the sled to be pushed down onto the plate and then slid to engage the sled channel with the sled flanges. The sled flanges may terminate some distance from the second end thereby enabling the sled to be placed proximal to the second end and then slid towards the first end of the bone plate for engagement with the sled flanges. The sled may have sled channel extensions that extend inward from either side of the sled channel. These sled channel extensions may extend under the sled flange to secure the sled down onto the bone plate. With this engagement, the sled can slide along the bone plate but can not be lifted up from the bone plate as the engagement of the sled flanges with the sled channel extensions prevents the sled from moving upward. This same arrangement may be employed by for the compression block, wherein the bone plate comprises a block flange configured to engage with the block channel and/or with block channel extensions that extend inward from the block channel.

An exemplary bone shortening osteotomy apparatus may further comprise a directional fastener aperture, a spanning fastener aperture as used herein, that can be accessed after recission of the bone and retraction of the cut bone ends toward each other. This spanning fastener aperture may be positioned for insertion of a spanning bone fastener from a second cut portion of bone into a first cut portion of bone, or across the two cut ends of the bones. This spanning fastener aperture may draw the first cut portion of bone toward the second cut portion of bone to further secure the two bone portions together and particularly the two cut ends, where close contact aids in rapid healing.

An exemplary bone plate may have stress sharing extensions that reduce sharp stress concentrations at the ends of the bone plate. The ends of the bone plate may be tapered for this purpose to provide some flexure of the ends to reduce high stress in these areas.

An exemplary bone plate may have a bottom recess that is configured over the retraced bone ends after the osteotomy procedure to allow the two cut bone ends room for growth and joining of the bone portions. The bottom recess may also allow for better imaging of the bone post procedure to determine healing progress and status of the bone in the excised area. The bottom recess may have a depth of about 1.0 mm or more, about 2 mm or more, about 3 mm or more, about 5 mm or more, or from about 1 to 5 mm and any other range between and including the bottom recess depths provided. The bottom recess may have a length of about 3 mm or more, about 5 mm or more, about 8 mm or more, about 10 mm or more, about 20 mm or more and any range between and including the bottom recess depths provided.

A jacking screw is coupled between the sled and the compression block and has threads for drawing the sled toward the compression block. In an exemplary embodiment, the threads of the jacking screw interface with a threaded aperture in the compression block and the head of the jacking screw is on an opposing side of the sled. The jacking screw may extend through a sled screw aperture, across a gap between the sled and compression block and into the block screw threaded aperture. It is to be understood that the jacking screw may be configured in an opposing orientation with the threaded end coupled with a threaded aperture in the sled.

An exemplary bone shortening osteotomy apparatus comprises a cutting guide that has one or more guide slots for guiding a cutting implement through the bone. The cutting guide may be detachably attachable to the bone shortening osteotomy apparatus, such as to the sled assembly. Any number of cutting guides may be used with various gaps between the guides slots for different procedures. The cutting guide may have a cutting guide alignment pin that extends out from the cutting guide and into an alignment pin aperture configured in the sled or compression block to reduce vibration of the cutting guide during cutting of the bone.

A slot wedge may be provided for insertion into a guide slot of a cutting guide and in some cases also into the slice cut out of a bone. After making the first cut through the bone, insertion of the slot wedge through guide slot and into the first cut will stabilize the bone during cutting of a second slice of the bone, wherein the cutting implement is inserted through a second guide slot. Also, the slot wedge secured in the guide slot and into the first cut will stabilize the cutting guide and reduce vibration when performing the second cut of bone through the second guide slot. A slot wedge may be substantially the same thickness as the width of a guide slot, or have a thickness that is at least 2 mm less than the width of the guide slot, or at least 1 mm less than the width of the guide slot, or at least 0.5 mm less than the width of the guide slot.

An exemplary bone shortening osteotomy apparatus comprises compression markings to indicate the amount of compression or retraction of the second cut portion of bone that is moved toward the first cut portion of bone via the sled assembly and jacking screw. Compression marking may be configured along the slotted aperture in the bone plate and/or along a sled guide pin.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
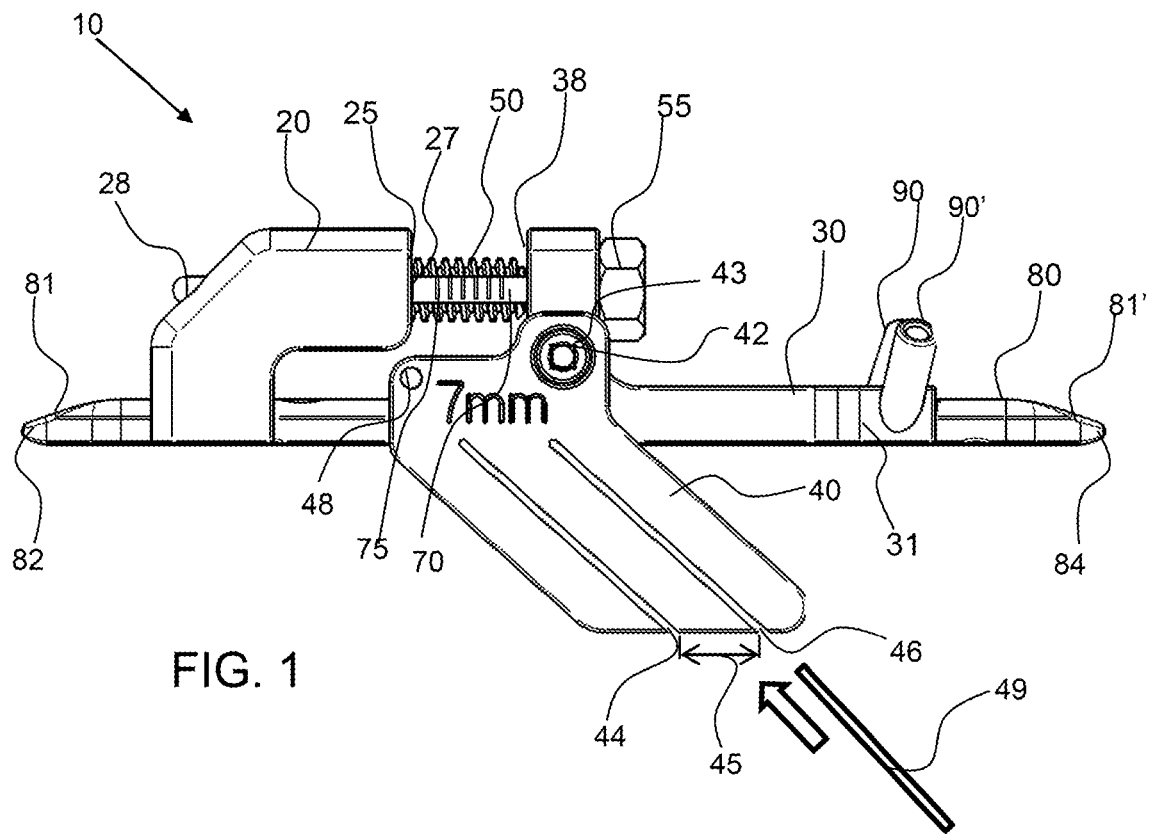
FIG. 1 shows a side view of an exemplary bone shortening osteotomy apparatus comprising a compression block and a sled assembly with a cutting guide, coupled to a bone plate.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is understood that where possible, features and components from one figure may be an included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments will occur to those skilled in the art and all such alternate embodiments, combinations, modifications, improvements are within the scope of the present invention.

Referring to FIGS. 1 to 6, an exemplary bone shortening osteotomy apparatus 10 comprises a compression block 20 and a sled assembly 30 with a cutting guide 40 coupled to a bone plate 80. A bone fastener may be inserted through the first end fastener aperture 87, and through the slotted aperture 88 into a bone to be shortened. K-wires are inserted through the K-wire barrels, 90, 90' and into the bone in a convergent angle to secure the bone plate to the bone and prevent twisting of the bone during retraction. The bone is cut using the cutting guide 40 by cutting through the bone using a cutting implement that is inserted into the first guide slot 44 and second guide slot 46. The gap distance 45 between first guide slot 44 and second guide slot 46 controls the excised length of bone. Any number of cutting guides may be provided with the bone shortening osteotomy apparatus with different gap distances; as shown, the gap distance is 7 mm for this exemplary cutting guide.

Figure 3:
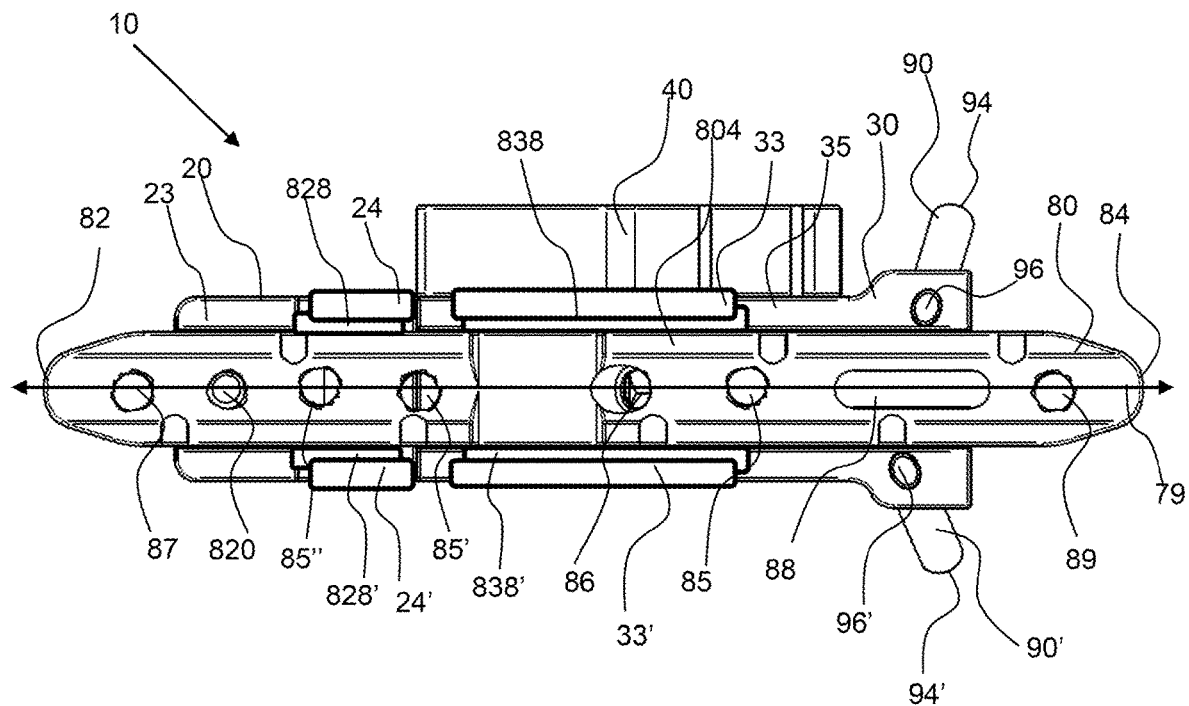
FIG. 3 shows a bottom view of the exemplary bone shortening osteotomy apparatus shown in FIG. 1 and a plurality of fastener apertures in the bone plate, including a slotted aperture, first and second end apertures, directional apertures and a spanning fastener aperture configured to receive and direct a fastener into the cut bone to draw the cut bone ends toward each other.

After the bone is secured to the bone plate by one or more fasteners extending through the bone plate 80 and into the bone on a first end 82 of the bone plate and by the fastener in the slotted aperture 88 the compression block 20 and sled assembly 30 may be coupled to the bone plate. The compression block may be configured with the compression block channel 23 extending down over at least a portion of the first side 808 and second side 809 of the bone plate 80. The compression block is secured to the bone plate 80 by a block fastener 28 that extends through the block fastener aperture 29, in the compression block, and into the plate-block threaded aperture 820 in the bone plate. This threaded aperture, the plate-block threaded aperture 820, enables the block fastener to secure the block directly to the bone plate. The block may also be retained to the bone plate by the block channel 23 extending around the bone plate and even more so by the block channel extensions 24, 24' that, as shown in FIG. 3, extend around the block flanges 828, 828' extending out from the bone plate. The block channel may be pushed down onto the bone plate and then the compression block can be slid along the bone plate to engage the block channel extensions with the block flanges. Note that the compression block may be coupled to the bone plate by the block flanges engaging with the block channel extension prior to the bone plate being coupled to the bone. The compression block will be slidably engaged with the bone plate and can be slid along the block channel extensions to enable insertion of fasteners through the bone plate and into the bone.

The sled assembly 30 may also be retained to the bone plate by the sled channel 35 extending down over at least a portion of the first side 808 and second side 809 of the bone plate 80. The first side and second side of the bone plate preferably extend parallel over at least over the portion of the length of the bone plate and particularly along the portion that the sled is configured to slide over the bone plate. The sled channel extensions 33, 33' as shown in FIG. 3, may extend around the sled flanges 838, 838' extending out from the bone plate. The sled 31 may be pushed down onto the bone plate to configure the sled channel around the bone plate, and then the sled assembly can be slid along the bone plate to engage the sled channel extensions with the sled flanges, such as from the second end toward the first end of the bone plate. Note that the sled assembly 30 may be coupled to the bone plate by the sled flanges engaging with the sled channel extension prior to the bone plate being coupled to the bone. The sled assembly will be slidably engaged with the bone plate and can be slid along the sled channel extension to enable insertion of fasteners and K-wires into the bone.

Figure 4:
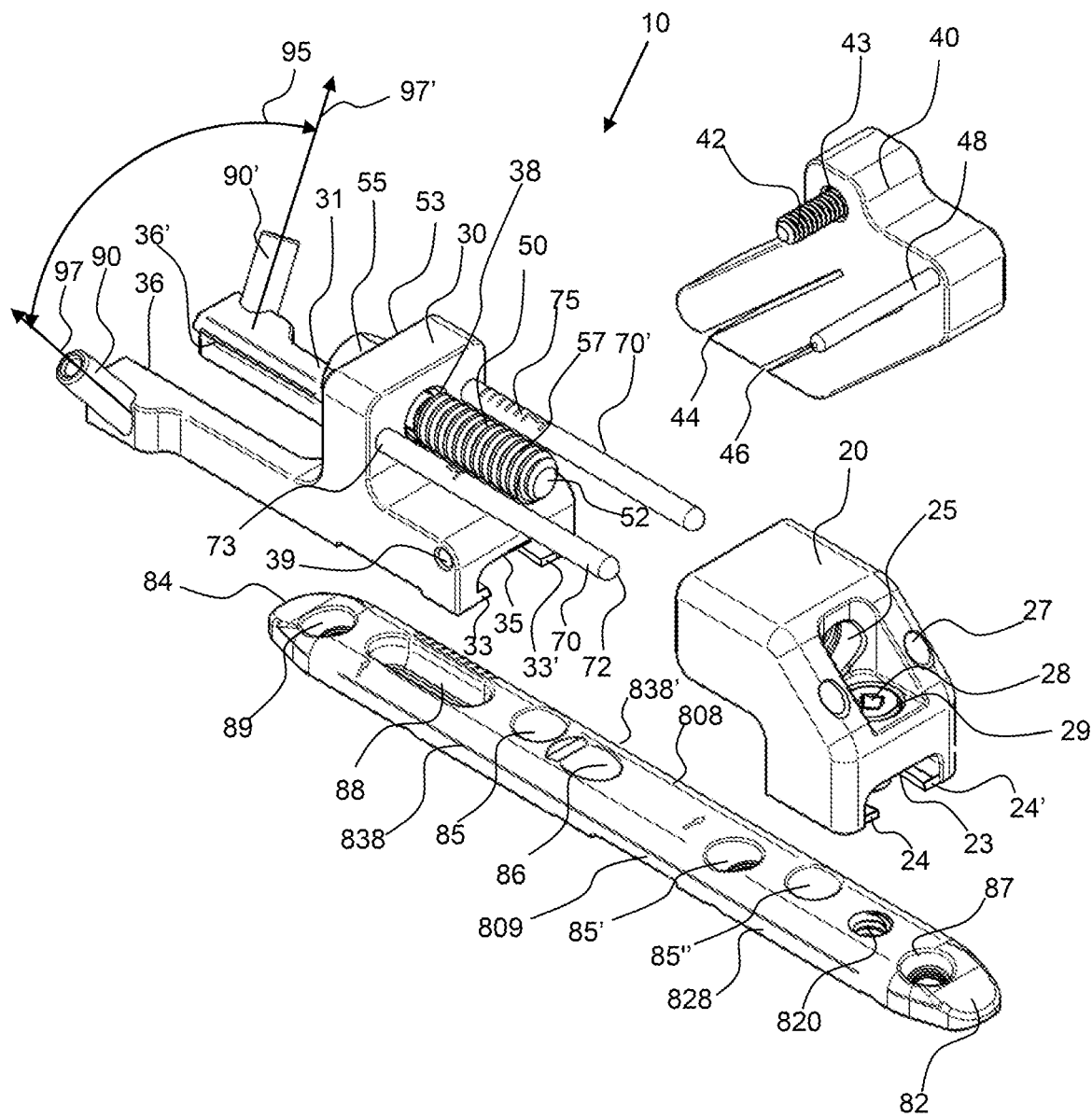
FIG. 4 shows a perspective view of the exemplary bone shortening osteotomy apparatus shown in FIG. 1 with the block and sled detached from the bone plate and the cutting guide detached from the sled.

The K-wires (not shown in FIG. 1-6) may be inserted through the K-wire barrels 90, 90' from an inlet opening 94 to the outlet opening 96 and into the bone. The K-wire barrels extend up from the sled 31 at a barrel angle 95 to allow effective penetration of the K-wires into the bone, as best shown in FIG. 4. The K-wires are convergent into the bone to prevent the sled and bone plate from lifting up from the bone. Referring to FIGS. 4 and 6, the K-wire barrels 90, 90' extend from an attached ends 92, 92' to the inlet opening 94, 94', respectively. Also, the K-wire barrels are convergent, wherein the inlet openings are further apart, or further away from the centerline of the bone plate than the outlet openings.

With the compression block and the sled assembly coupled to the bone plate, and after a portion of the bone is excised using the cutting guide 40, the turning interface 55 of the jacking screw 50, can be turned to draw the sled 31 toward the compression block 20 and the second cut portion bone, secured to the sled by the K-wires, toward the first cut portion of bone, secured to the compression block by fasteners. The bone fastener configured in the slotted aperture moves within the slotted aperture 88 to keep the bone in alignment during the retraction. The turning interface 55, such as a screw head or bolt head 56, is turned by a turning implement, such as a wrench, including an Allen wrench, socket wrench or screw driver, until the second cut bone end is retracted to an effective position with respect to the first cut bone end. The compression markings 75 on the sled guide pin 70 and or the plate compression marking 83 may be used to monitor and measure the amount of retraction. The sled guide pins 70, 70' are coupled with the sled assembly 30 and slide into block pin apertures 27 in the compression block 20. A bone fastener may then be inserted through the spanning bone fastener aperture 86 at an angle to secure the two cut ends of the bone together. A spanning fastener extends from the second cut portion of bone across the first and second cut bone ends and into the first cut portion of bone to retain and further drawn the two cut bone ends together. Additional fasteners may then be inserted through fastener apertures, such as directional fastener apertures to secure the bone plate to the bone. The K-wires may then be removed along with the cutting guide 40, sled assembly 30 and compression block 20. Some additional bone fasteners may be inserted into fastener apertures after the removal of these components as these fastener apertures may have been blocked by the sled assembly or compression block.

As best shown in FIG. 1, the cutting guide 40 is coupled to the sled 31 by a cutting guide fastener 42 that extends through a cutting guide fastener aperture 43 in the cutting guide and into a threaded aperture in the sled. The cutting guide has a first guide slot 44 and a second guide slot 46 spaced apart by a gap distance 45. A plurality of cutting guides may be provided with different gap distances 45 between the first and second guide slots. A slot wedge 49 may be part of the exemplary bone shortening osteotomy apparatus 10 and is configured for insertion into a guide slot after cutting the bone. The slot wedge extends through the guide slot after the first cut is made and the cutting implement is removed. The slot wedge may extend through the first guide slot and into the slice cut out of the bone to stabilize the bone while the bone is cut through the other guide slot. The slot wedge may help to prevent the bone from becoming misaligned and stabilize the cutting guide while making the second cut in the bone with a cutting implement extending through the second guide slot. As shown in FIG. 4, the cutting guide has a cutting guide alignment pin 48 that is configured to extend into alignment pin aperture 39 in the sled assembly 30.

The bone plate 80 has tapered end portions 81, 81' to allow for effective load sharing between the bone plate and the bone. The tapered end portions 81, 81' taper to the extended ends of the bone plate, or to the first end 82 and second end 84, respectively. The tapered end portions taper in thickness, and also in width toward the end of the bone plate 80.

Figure 2:
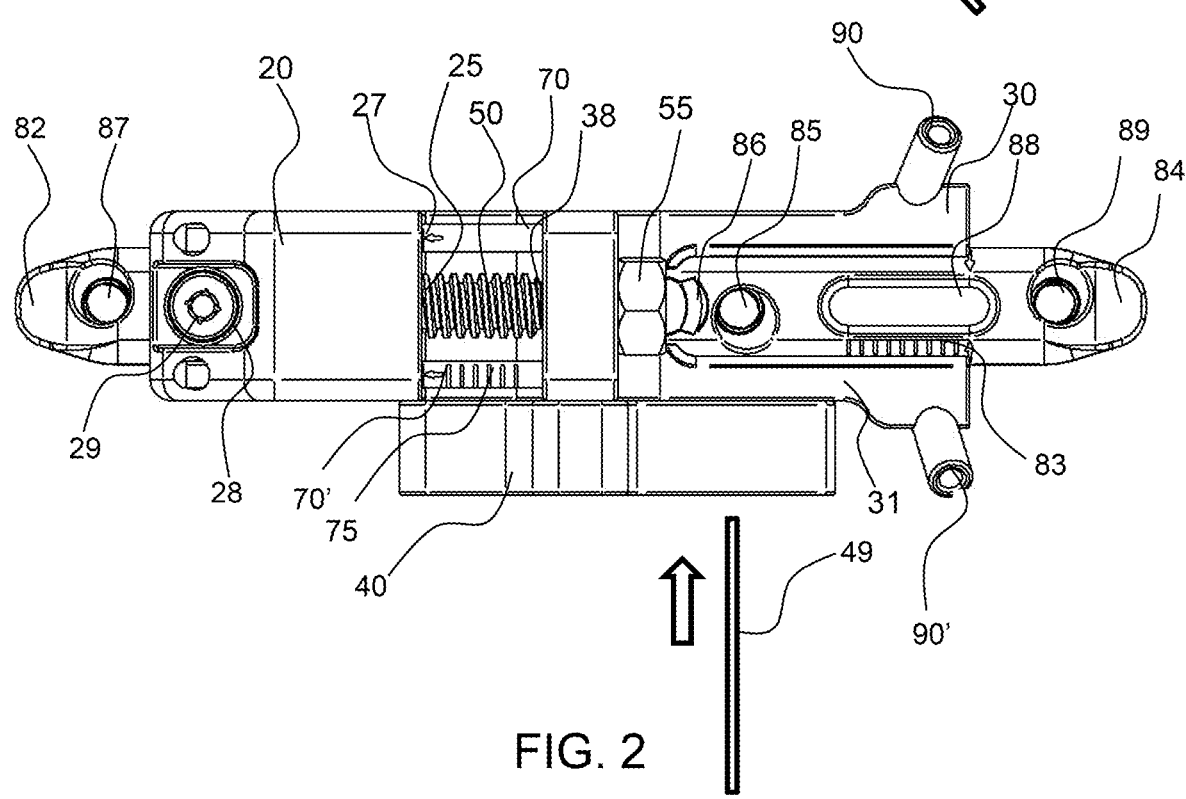
FIG. 2 shows a top view of the exemplary bone shortening osteotomy apparatus shown in FIG. 1 and a plurality of fastener apertures in the bone plate including a slotted aperture that enables the cut bone to be retracted toward the compression block by tightening of the jacking screw into the block.

As shown in FIG. 2, a spanning bone fastener aperture 86 is configured to receive a bone fastener, a lag screw for example, therethrough after the bone is retracted. This enables stabilizing the bone with the fastener extending across the cut between the first cut bone end and second cut bone end before the block and sled are removed. The bone plate also has a first end fastener aperture 87 and a second end fastener aperture 89 configured proximal to the first end 82 and second end 84 of the bone plate, respectively. The bone plate also has a slotted aperture 88 and additional directional bone fastener apertures 85-85" that direct a fastener at an offset angle into the bone. The first end and second end fastener apertures may be direction apertures. The sled has K-wire barrel extensions that extend toward the second end 84 of the bone plate and have a slot to provide access to the slotted aperture 88, at least one directional bone fastener aperture 85 and to the spanning bone fastener aperture 86. This allows insertion of bone fastener to retain the second cut portion of bone to the bone plate after retraction of the bone.

As shown in FIG. 3, the K-wire barrels 90, 90' are configured to direct K-wires into a bone to secure the bone to the sled assembly 30. The bone plate has a slotted aperture 88 for receiving a bone fastener into the second cut portion of bone that is retracted toward the compression block. The bone plate has a plate-block threaded aperture 820 to secure the compression block 40 in a fixed position to the bone plate 80. The bone plate also has a plurality of directional bone fastener apertures 85-85" configured to direct fasteners into the bone at offset angles. The bone plate has a plurality of bone fastener aperture for receiving bone fasteners therethrough. The bone plate has a length from the first end 82 to the second end 84 as measure along the length axis 79 extending in a straight line between the first and second ends of the bone plate.

As shown in FIGS. 3 and 4, an exemplary bone plate has a pair of sled flanges 838, 838' for engaging with the sled channel extensions 33, 33' of the sled channel 35 to retain the sled in slidable engagement with the bone plate. The sled channel 35, as best shown in FIG. 4, is configured to fit over the top and down along the first side 808 and second side 809 of the bone plate. The channel extensions 33, 33' extend inward toward the opposing side of the bone plate to engage with the sled flanges 838, 838' extending from the bone plate. The sled flanges and the block flanges may be configured proximal a bottom of the bone plate and extend outward from the first and second side of the bone plate The sled flanges may be configured along a portion of the bone plate that the sled will move during the procedure of retracting the cut bone portions together. The sled flanges may not extend to the second end 84 of the bone plate 80 to enable the sled to be configured down onto the bone plate and then slid towards the first end 82 of the bone plate to engage the sled channel extensions 33, 33' with and under the sled flanges 838, 838' of the bone plate. With this engagement, the sled can slide along the bone plate but can not be lifted up from the bone plate as the sled flanges prevent the sled channel from moving upward. This same arrangement may be employed for the compression block, wherein the bone plate comprises block flanges 828, 828' extending from opposing sides of the bone plate and wherein the compression block comprises block channel extension 24, 24' extending from the block channel 23 (shown in FIG. 4) to engage with the block flanges. Again, the block flanges may not extend to the first end 82 of the bone plate to allow the block to be configured over the bone plate and then slid toward the second end 84 to engage the block flanges with and under the block channel extensions. The compression block 20 is detachably attached to the bone plate 80 by the block fastener 28 that extends through the block fastener aperture 29 and into the plate-block threaded aperture 820. The compression block also has a block channel 23 configured to receive the bone plate 80. The block channel has side extensions that extend down over at least a portion of the sides of the bone plate.

With continued reference to FIG. 4, the sled assembly 30 is configured with sled extensions 36, 36' configured to extend around the sides of the bone plate 80 to retain the sled linearly along the length of the bone plate while enabling the sled to slide along the length of the bone plate. The sled extensions form an opening in the top of the sled assembly to allow access to the slotted aperture 88 in the bone plate.

The sled guide pins 70, 70' are configured on opposing sides of the jacking screw 50 to ensure alignment of the movement of the sled and second cut bone coupled thereto during retraction. The sled guide pin 70 has compression markings 75 to monitor and measure the amount of retraction. The sled guide pins 70, 70' are coupled with the sled 31 and extend into block pin apertures 27 to guide the sled during retraction of the cut bone. The sled guide pins have a sled end 73, coupled with the sled, and a block end 72 that is inserted into the block pin apertures for alignment.

The jacking screw extends from a sled end 53, having a turning interface 55, through the sled-screw aperture 38 to the block end 52 of the jacking screw. The jacking screw has a threaded portion having threads 57 configured to extend into the block-screw threaded aperture 25 to draw the sled assembly toward the compression block 20. The sled guide pins 70, 70' slide into the block-pin apertures 27 as the sled slides over the bone plate 80.

The cutting guide 40 is detachably attachable to the sled by the cutting guide fastener 42 that extends through the cutting guide fastener aperture 43 and into a sled-guide threaded aperture in the sled. The cutting guide may be configured for insertion on either side of the sled assembly 30. The cutting guide also has a cutting guide alignment pin 46 that extends into the alignment pin aperture 39 of the sled to provide some stability of the cutting guide during cutting. When the cutting implement is moved through the guide slots it can cause the cutting guide to vibrate and the alignment pin secured in the alignment pin aperture may reduce this vibration.

As best shown in FIG. 4, the K-wire barrels 90, 90' are configured on opposing sides of the sled 31 and on a distal end of the sled assembly 30, or second end, from the compression block and they are convergent, having a barrel angle 95, wherein the inlet openings are further apart than the outlet opening. As described herein, this converging arrangement or non-parallel arrangement of the K-wire barrels retains the sled to the bone plate as the K-wires produce a retaining force when inserted in the bone through the converging K-wire barrels. The barrel angle 95 is the angle between conduit axes 97, 97' of the K-wire barrels.

Figure 5:
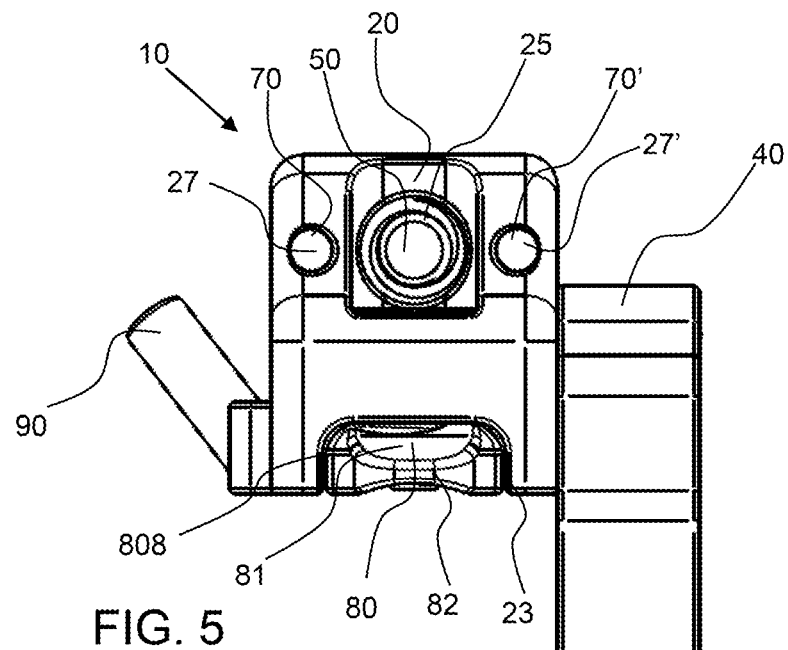
FIG. 5 shows a first end view of the exemplary bone shortening osteotomy apparatus shown in FIG. 1.
Figure 6:
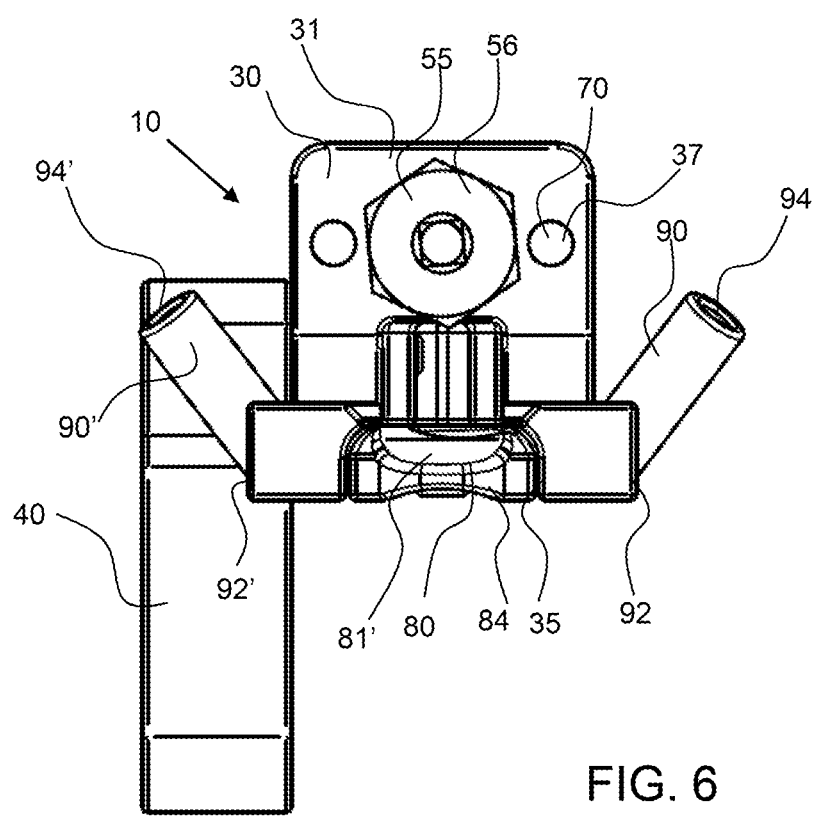
FIG. 6 shows a second end view of the exemplary bone shortening osteotomy apparatus shown in FIG. 1.

Referring now to FIGS. 5 and 6, the bone plate 80 is configured in the block channel 23 of the compression block 20. The cutting guide 40 is coupled to the sled assembly 30 along with the K-wire barrels 90 that extend at a barrel angle 95, as shown in FIG. 4, to enable penetration and retention of the bone when the sled is drawn toward the compression block. As shown in FIG. 6, the bone plate 80 is configured in the sled channel 35 to enable the sled to move along the length of the bone plate and maintain alignment with the bone plate. The turning interface 55 of the jacking screw 50, may be a bolt head 56, having a plurality of planar surfaces to enable engagement with a wrench or socket wrench to turn the jacking screw. The K-wire barrels 90 extend at a barrel angle to enable penetration and retention of the sled to the bone during retraction and to produce convergent K-wires into the bone.

Figure 7:
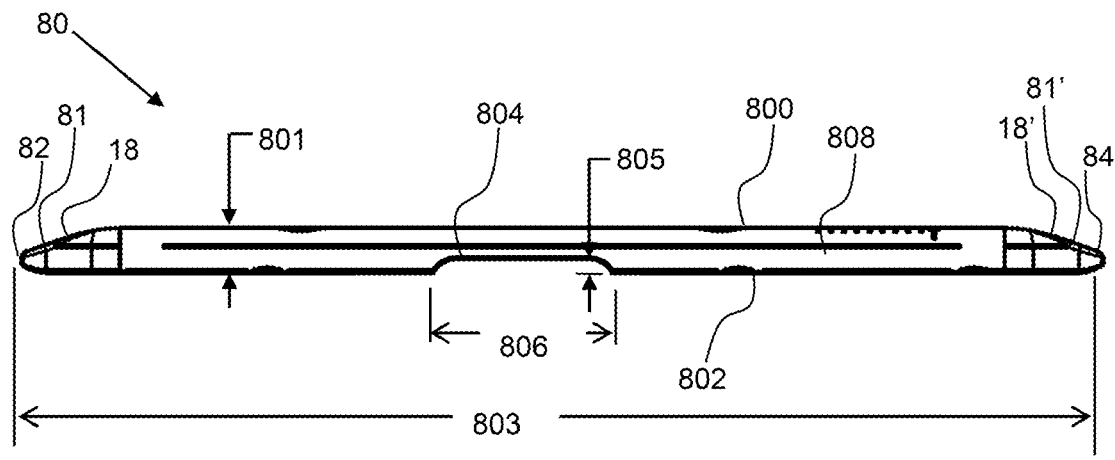
FIG. 7 shows a first side view of an exemplary bone plate having stress sharing extensions on both the first and second ends and a bottom recess to aid in cutting through the bone for excision of a segment of the bone and for clear viewing of the bone after the osteotomy procedure.

As shown in FIG. 7, the exemplary bone plate 80 has length 803 from a first end 82 to a second end 84, a thickness 801 from a top side 800 to a bottom side 802 and a bottom recess 804 having a recess depth 805 and recess length 806 to aid in cutting through the bone for excision of a segment of the bone and for clear viewing of the bone after the osteotomy procedure to shorten the bone. The bone plate has a stress sharing extensions 18, 18', comprising a tapered end portion 81, 81' on the first end 82 and second end 84, respectively. These stress sharing extensions taper toward the ends to allow some flexibility and load sharing between the ends of the bone plate and the bone. The tapered end portions taper in the thickness 801 dimension of the bone plate 80.

Figure 8:
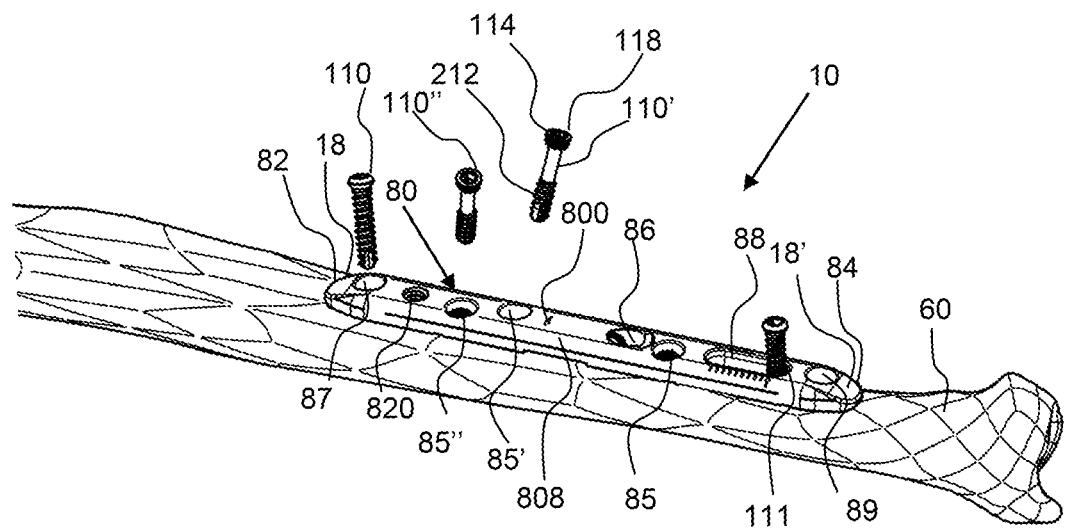
FIG. 8 shows a perspective view of an exemplary bone plate of an exemplary bone shortening osteotomy apparatus being coupled to a bone with a plurality of bone fasteners configured to extend through the bone fastener apertures of the plate on the first end and a single bone fastener configured in the slotted aperture on the second end of the bone plate.
Figure 10:
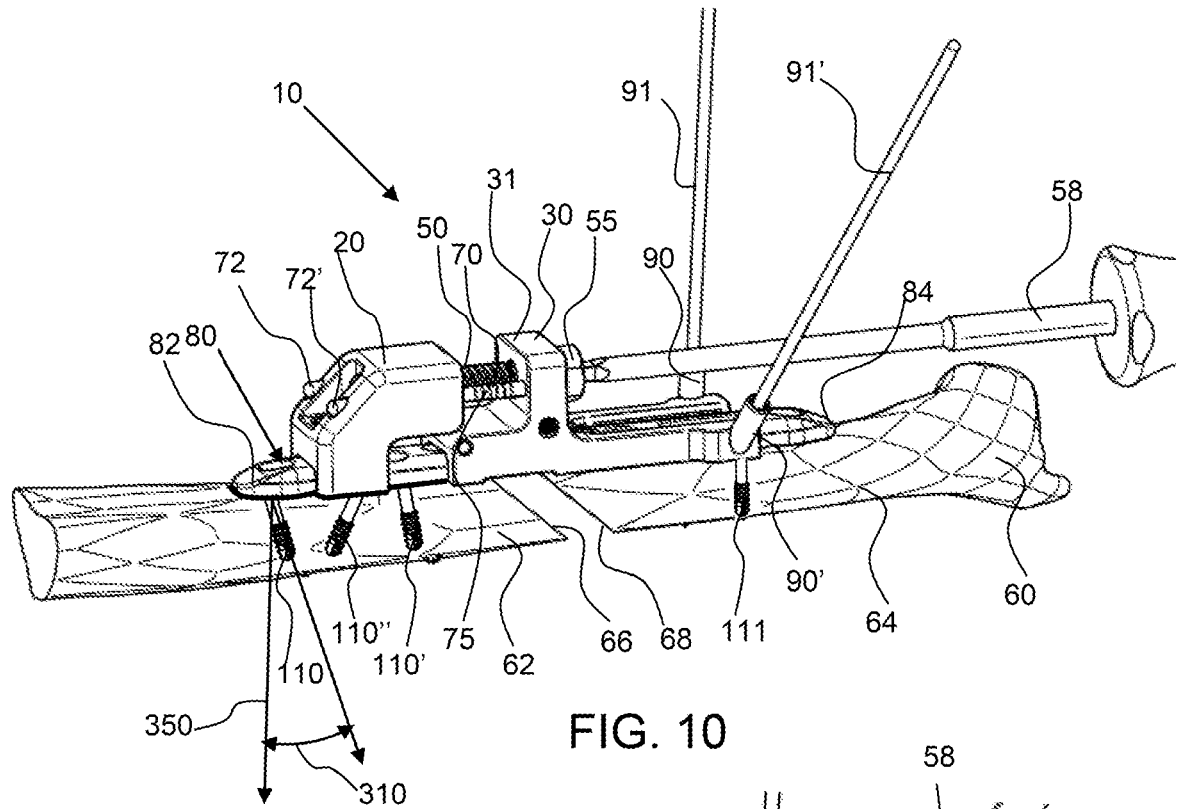
FIG. 10 shows a perspective side view of the exemplary bone plate shown in FIG. 9, coupled to the bone with the compression block and sled assembly of the bone shortening osteotomy apparatus coupled to the bone plate with a portion of the bone excised to produce a first cut portion of bone with a first cut bone end and a second cut portion of bone with a second cut bone end, and with the sled being drawn toward the compression block by the jacking screw.

As shown in FIG. 8, an exemplary bone plate 80, of an exemplary bone shortening osteotomy apparatus 10, is being coupled to a bone 60 with a plurality of bone fasteners, 110, 110', 110" configured to extend through the bone fastener apertures proximal to the first end 82 of the bone plate, or end of the bone plate that extends over the first cut portion of bone after the cut is made in the bone, as shown in FIG. 10. Bone fastener 110 is configured to extend through the first end bone fastener aperture 87 and bone fasteners 110' and 110" are configured to extend through directional bone fastener apertures 85', 85" respectively. A single slotted bone fastener 111 is configured in the slotted aperture 88 proximal to the second end 84 of the bone plate, or end of the bone plate that extends over the second cut portion of bone after the cut is made in the bone, as shown in FIG. 10. The slotted bone fastener 111 in the slotted aperture is configured proximal to the second end of the slot to allow the fastener to slide within the slotted aperture as the second cut bone portion is retracted toward the first cut bone portion or toward the compression block. Fasteners 110' and 110" extend through directional bone fastener apertures 85,' 85" respectively, and direct the fasteners in an offset angle to vertical through the bone plate. Vertical, as used herein, is normal to the plane of the bone plate, or top side in most cases. Note that one or more of the fasteners may have bone threads 212 configured on an extended end of the bone fastener and plate threads 114, configured proximal to the fastener head 118 and configured to secure the fastener to the bone plate or an insert configured in the bone plate fastener aperture. A fastener may be inserted through the second end bone fastener aperture 89 after the second cut portion of bone is retracted to the first cut portion of bone. The fasteners extend through the bone plate from a top surface 800 of the bone plate. The bone fastener 110, a far cortical fastener, may be inserted first as this fastener has threads along the length and is retained in the far cortical portion of the bone as well as the near cortical to aid in load sharing with the bone plate. The slotted bone fastener 111 may then be configured in the slotted aperture 88 followed by the two directional fasteners 110' and 110". The direction fasteners may be non-parallel and may extend through the bone plate in a convergent orientation as described herein. After these fasteners are inserted, the compression block and sled assembly can be coupled to the bone plate.

Figure 9:
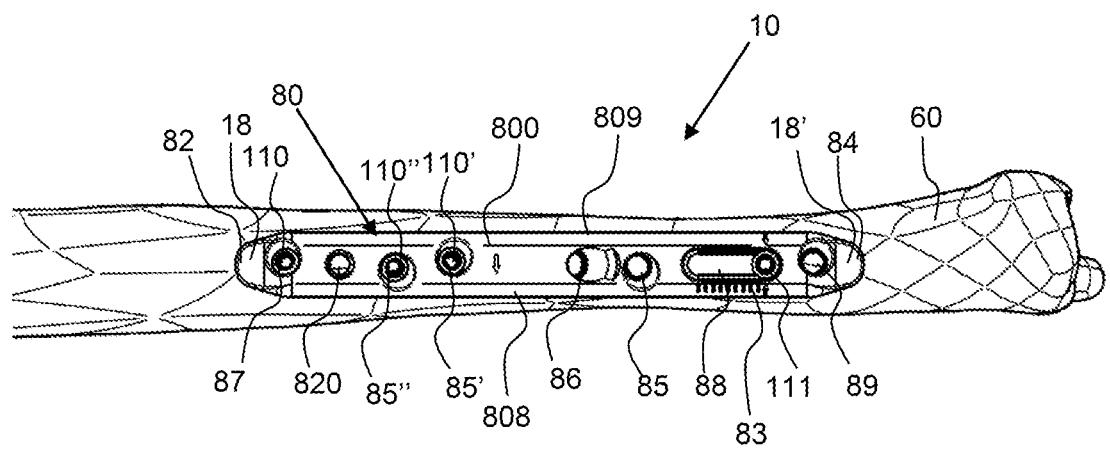
FIG. 9 shows a top view of an exemplary bone plate shown in FIG. 8, now coupled to the bone with a plurality of bone fasteners configured through the bone fastener apertures of the plate on the first end and a single bone fastener configured in the slotted aperture on the second end of the bone plate.
Figure 11:
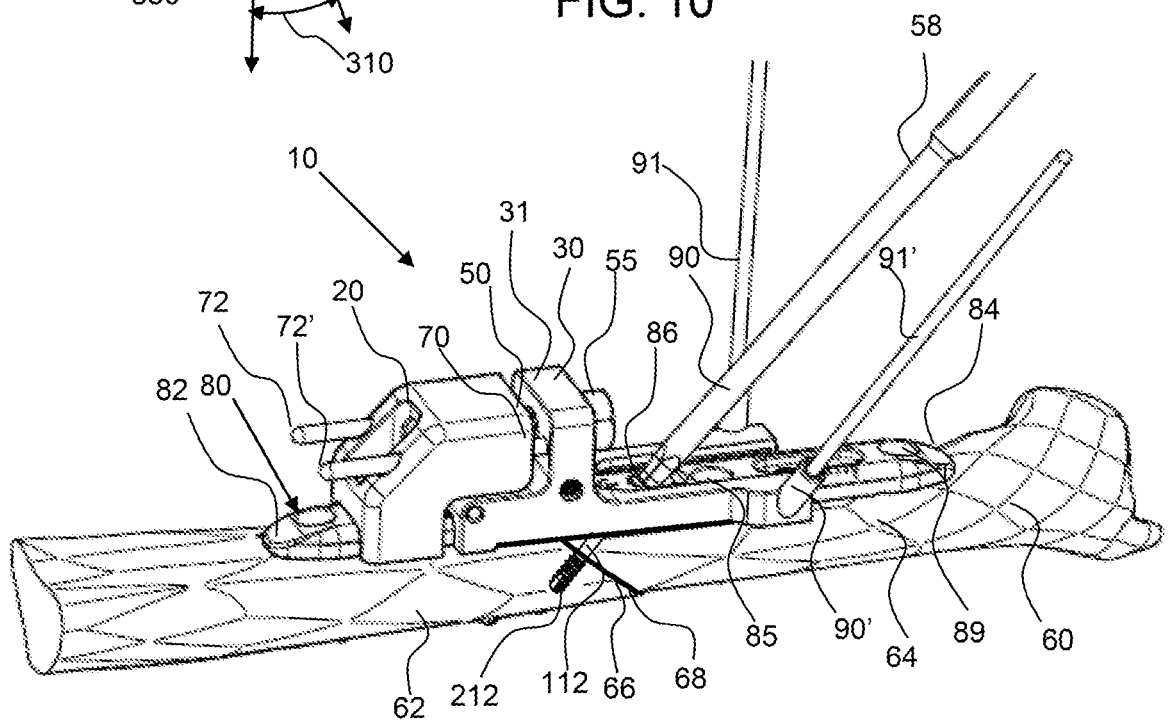
FIG. 11 shows a perspective side view of the exemplary bone plate shown in FIG. 10, with the sled now drawn to retract the first cut portion of bone and first cut bone end to the second cut portion of bone and second cut bone end, and with the a spanning fastener configured in the spanning fastener aperture and being inserted from the second cut portion of bone into the first cut portion of bone across the first and second cut bone ends.
Figure 12:
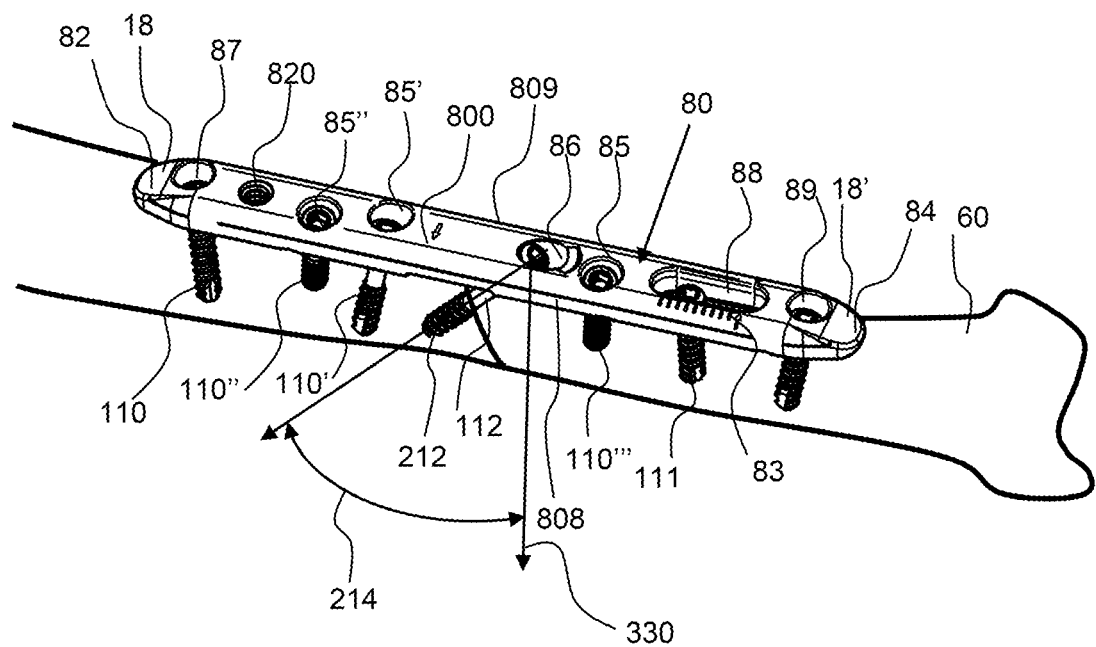
FIG. 12 shows a perspective side view of the bone plate show in FIG. 11, with the compression block and sled assembly removed and the two cut bone portions secured together by the bone plate and fasteners.

As shown in FIG. 9, the fasteners are now secured through the bone plate 80 and into the bone 60. Again, the slotted bone fastener 111 in the slotted aperture 88 is configured proximal to the second end of the slot to allow the fastener to slide within the slotted aperture as the second cut bone portion is retracted toward the first cut bone portion or toward the compression block Referring now to FIGS. 10 and 11, an exemplary bone shortening osteotomy apparatus 10, now has the compression block 20 secured to the bone plate 80 by a fastener and the sled 31 of the sled assembly 30 configured over the bone plate with the sled channel extending around the sides of the bone plate. A portion of the bone plate has been excised to leave a gap between the first cut bone portion 62 and the second cut bone portion 64. The jacking screw 50 extends through the sled screw aperture and into the block screw threaded aperture such that when the jacking screw is rotated by the turning interface 55 with the turning implement 58, a screwdriver in this embodiment, the sled assembly moves toward the compression block. Two K-wires 91, 91' are configured through the K-wire barrels 90, 90' of the sled assembly and retain and force the second cut portion of bone 64 toward the first cut portion of bone 62 as the sled assembly is retracted toward the compression block 20. The second cut bone end 68 is brought into close proximity or contact with the first cut bone end 66, as shown in FIG. 11, before the spanning bone fastener 112 is inserted through the spanning bone fastener aperture 86 to further draw the first cut bone end and second cut portion of bone toward the first cut portion of bone and first cut bone end. This spanning bone fastener has bone threads 212 to pull the first cut portion of bone toward the second cut portion of bone, as shown in FIG. 12. Additional bone fasteners on the second end of the bone plate can then be inserted to further secure the second cut portion of bone 64 to the bone plate such as in directional bone fastener aperture 85 and the second end fastener aperture 89, as shown best shown in FIGS. 8 and 9.

FIG. 12 shows a perspective top-side view of the bone plate show in FIG. 11, with the compression block and sled assembly removed and the two cut bone portions secured together by the bone plate and the plurality of bone fasteners 110, 110', 110", 110''', 110'''' extending into the bone 60. Any of these bone fasteners may be directional fasteners that extend at an offset angle 310 with respect to a vertical axis 350, which is an axis that is normal to the length axis of the bone plate, and down from a top side of the bone plate, as shown in FIG. 10. The directional bone apertures and directional bone fasteners may extend from a first end toward a second end of the bone plate or may extend from a first side toward a second side of the bone plate or vice versus or a combination thereof. The spanning bone fastener 112 is configured to extend at a spanning angle 214 as directed by the spanning bone fastener aperture 86 in the bone plate 80. The spanning angle 214 is the angle from a normal plane 330 with respect to length axis of the bone plate. The spanning angle may be about 20 degrees or more, about 30 degrees or more, about 45 degrees or more, about 60 degrees or more, about 75 degrees or less and any range between and including the spanning angles provided.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of shortening a bone comprising:
   a) providing a bone shortening osteotomy apparatus comprising:
      i) a bone plate extending a length along a length axis from a first end to a second end, said bone plate comprising;
      a first side and a second side opposing said first side;
      a spanning bone fastener aperture;
      a first end bone fastening aperture configured more proximal to the first end of the bone plate than the spanning bone fastener aperture;
      a slotted fastener aperture configured more proximal to said second end of the bone plate than the spanning bone fastener aperture;
      a second end bone fastening aperture configured more proximal to the second end of the bone plate than the spanning bone fastener aperture;
      a plate-block threaded aperture;
      ii) a single jacking screw comprising:
      a sled end;
      a block end;
      a turning interface; and
      threads;
      iii) a sled assembly that is detachably coupled with the bone plate; said sled assembly comprising:
      a sled;
      a sled channel configured to extend over a portion of the first side and second side the bone plate; and
      a pair of K-wire barrels each configured to receive a K-wire therethrough and into said bone;
      wherein the K-wire barrels are non-parallel from an opening end to an outlet end; and
      wherein the K-wire barrels extend at a barrel angle that is at least 20 degrees;
      iv) a block fastener;
      v) a compression block that is detachably attached to the bone plate,
      wherein said block fastener is configured for insertion through a block fastener aperture through the compression block and into said plate-block threaded aperture, said compression block comprising a block screw aperture configured to receive the block end of the jacking screw; wherein the sled end of the jacking screw is coupled with the sled;

vi) a pair of sled guide pins configured on opposing sides of the single jacking screw and configured to extend between the sled assembly and the compression block, wherein each of said sled guide pins is configured to linearly translate within and with respect to the compression block; and vii) a cutting guide coupled with the sled assembly and comprising:
a first guide slot; and
second guide slot;

b) attaching the compression block to the bone plate by inserting the block fastener through the block fastener aperture in the compression block and into the plate-block threaded aperture in the bone plate;

c) coupling the sled assembly to the bone plate by configuring the sled channel over the bone plate by coupling the pair of sled guide pins between the sled assembly and the compression block;
wherein the sled channel aligns the sled assembly over the bone plate;
wherein the single jacking screw extends from the sled assembly to the compression block generally parallel with the length axis of the bone plate; and
wherein the single jacking screw extends from the sled into the block screw aperture of the compression block;

d) configuring the bone plate over said bone;

e) securing the bone plate to said bone by inserting a first end bone fastener through the first end bone fastening aperture and into said bone;

f) inserting a slotted bone fastener through the slotted fastener aperture and into said bone;

g) inserting K-wires through the pair of K-wire barrels and into the bone;

h) cutting a bone portion for resection using a cutting implement inserted through the first guide slot to produce a first cut in said bone and through the second guide slot to produce a second cut in said bone;

i) resecting the bone portion to produce a first cut bone end on a first cut portion of bone and a second cut bone end on a second cut portion of bone;

j) turning the single jacking screw to move the sled assembly toward the compression block, wherein said K-wires force the second cut end toward the first cut end;

k) inserting a spanning bone fastener through the spanning bone fastener aperture;
wherein the spanning bone fastener extends from the second cut portion of bone across the second cut bone end and into the first cut portion of bone across the first cut bone end;

l) securing the second cut portion of bone to the bone plate by inserting a second end bone fastener through said second end fastening aperture and into the second cut portion of bone;

m) removing the K-wires; and n) removing the compression block and the sled assembly.

2. The method of claim 1, wherein the bone plate comprises a directional aperture and wherein a directional bone fastener is inserted through the directional aperture and into the bone at an offset angle.

3. The method of claim 2, wherein the directional bone fastener extends through the directional aperture from the second end of the bone plate toward the first end of the bone plate.

4. The method of claim 2, wherein the directional bone fastener extends into the first cut portion of bone.

5. The method of claim 2, wherein the first end bone fastening aperture is a directional aperture.

6. The method of claim 1, wherein the turning interface of the jacking screw comprises a head and wherein the head is configured on the sled end of the jacking screw.

7. The method of claim 6, wherein the sled further comprises a sled screw aperture extending through said sled and wherein the jacking screw extends through said sled screw aperture, wherein the block screw aperture comprises threads and wherein the threads of the jacking screw engage with the threads of the block screw aperture.

8. The method of claim 1, wherein the K-wire barrels extend at a barrel angle that is at least that is at least 60 degrees.

9. The method of claim 8, wherein the K-wire barrels are configured on opposing sides of the sled assembly.

10. The method of claim 1, wherein the bone plate further comprises a bottom recess extending along a portion of a bottom of the bone plate and aligned with the cutting guide, and wherein the cutting implement extends into said bottom recess during cutting a bone portion.

11. The method of claim 1, wherein the cutting guide is detachably attachable to the sled assembly;
wherein the cutting guide has a cutting guide fastener aperture for receiving a guide-sled fastener therethrough and wherein the sled assembly further comprises a sled-guide threaded aperture for receiving the guide-sled fastener therein.

12. The method of claim 11, wherein the sled has an alignment pin aperture and wherein the cutting guide has an alignment pin that is configured to extend into said alignment pin aperture.

13. The method of claim 1, wherein the compression block comprises a block channel configured to extend over a portion of the first side and second side the bone plate.

14. The method of claim 13, wherein the bone plate comprises block flanges extending from the opposing first and second sides of the bone plate and wherein the block channel comprises block channel extensions configured to engage with the block flanges to retain the compression block to the bone plate, and
wherein attaching the compression block to the bone plate includes configuring the block channel extensions below the block flanges and then sliding the compression block to position the block channel extension under the block flanges with respect to a top side of the bone plate to retain the compression block to the bone plate.

15. The method of claim 1, wherein the spanning bone fastener aperture extends at a spanning angle of at least 30 degrees from a normal plane to the length axis of the bone plate, wherein the length axis extends from said first end to said second end of the bone plate, and wherein the spanning bone fastener aperture is configured to direct the spanning bone fastener toward said first end of the bone plate.

16. A method of shortening a bone comprising:
a) providing a bone shortening osteotomy apparatus comprising:
i) a bone plate comprising:
a length extending along a length axis from a first end to a second end;
a first side and a second side opposing said first side;
a spanning bone fastener aperture;
a first end bone fastening aperture configured more proximal to the first end of the bone plate than the spanning bone fastener aperture;

a slotted fastener aperture configured more proximal to said second end of the bone plate than the spanning bone fastener aperture;
a second end bone fastening aperture configured more proximal to the second end of the bone plate than the spanning bone fastener aperture;
a plate-block threaded aperture;
ii) a single jacking screw comprising:
a sled end;
a block end;
a turning interface;
threads;
iii) a sled assembly that is detachably coupled with the bone plate; said sled assembly comprising:
a sled;
a sled channel configured to extend over a portion of the first side and second side the bone plate;
a pair of K-wire barrels each configured to receive a K-wire therethrough and into said bone;
wherein the K-wire barrels extend non-parallel to each other;
iv) a block fastener;
v) a compression block that is detachably attached to the bone plate,
wherein said block fastener is configured for insertion through a block fastener aperture through the compression block and into said plate-block threaded aperture, said compression block comprising:
a block screw aperture configured to receive the block end of the jacking screw; wherein the sled end of the jacking screw is coupled with the sled;
vi) a pair of sled guide pins configured on opposing sides of the single jacking screw and configured to extend between the sled assembly and the compression block, wherein each of said sled guide pins is configured to linearly translate within and with respect to the compression block;
vii) a cutting guide coupled with the sled assembly and comprising:
a first guide slot; and
second guide slot;
viii) a slot wedge, and wherein said slot wedge is configured for insertion through the first guide slot and into a first cut of said bone;
b) attaching the compression block to the bone plate by inserting the block fastener through the block fastener aperture in the compression block and into the plate-block threaded aperture in the bone plate;
c) coupling the sled assembly to the bone plate by configuring the sled channel over the bone plate; wherein the sled channel aligns the sled assembly over the bone plate, and
coupling the pair of sled guide pins between the sled assembly and the compression block,
wherein the single jacking screw extends from the sled assembly to the compression block generally parallel with the length axis of the bone plate;
wherein the single jacking screw from the sled extends into the block screw aperture of the compression block;
d) configuring the bone plate over said bone;
e) securing the bone plate to said bone by inserting a first end bone fastener through the first end bone fastening aperture and into said bone;
f) inserting a slotted bone fastener through the slotted fastener aperture and into said bone;
g) inserting K-wires through the pair of K-wire barrels and into the bone;

h) cutting a bone portion for resection using a cutting implement inserted through the first guide slot to produce a first cut in said bone, the cutting comprising:
i) inserting the slot wedge through the first guide slot and into the first cut of said bone;
ii) inserting the cutting implement through the second guide slot to produce a second cut in said bone;
wherein the slot wedge stabilizes the cutting guide while the second cut in said bone is produced;
i) resecting the bone portion to produce a first cut bone end on a first cut portion of bone and a second cut bone end on a second cut portion of bone;
j) turning the single jacking screw to move the sled assembly toward the compression block, wherein said K-wires force the second cut end toward the first cut end;
k) inserting a spanning bone fastener through the spanning bone fastener aperture;
wherein the spanning bone fastener extends from the second cut portion of bone across the second cut bone end and into the first cut portion of bone across the first cut bone end;
l) securing the second cut portion of bone to the bone plate by inserting a second end bone fastener through said second end fastening aperture and into the second cut portion of bone;
m) removing the K-wires; and
n) removing the compression block and the sled assembly.

17. The method of claim 1, wherein each of the sled guide pins have a sled end coupled with the sled and a block end; and
wherein the compression block comprises a pair of block pin apertures having the block ends of the pair of sled guide pins configured therein,
wherein the pair of sled guide pins slide into the block pin apertures when the sled assembly moves toward the compression block.

18. The method of claim 17, wherein at least one of the pair of sled guide pins has compression markings.

19. A method of shortening a bone comprising:
a) providing a bone shortening osteotomy apparatus comprising:
i) a bone plate comprising:
a length extending along a length axis from a first end to a second end;
a first side and a second side opposing said first side;
a spanning bone fastener aperture;
a first end bone fastening aperture configured more proximal to the first end of the bone plate than the spanning bone fastener aperture;
a slotted fastener aperture configured more proximal to said second end of the bone plate than the spanning bone fastener aperture;
a second end bone fastening aperture configured more proximal to the second end of the bone plate than the spanning bone fastener aperture;
a plate-block threaded aperture;
sled flanges extending from the opposing first side and the second side of the bone plate;
ii) a single jacking screw comprising:
a sled end;
a block end;
a turning interface;
threads;
iii) a sled assembly that is detachably coupled with the bone plate; said sled assembly comprising:
a sled;

a sled channel configured to extend over a portion of the first side and second side the bone plate;

sled channel extensions configured to engage with the sled flanges to retain the sled to the bone plate;

a pair of K-wire barrels each configured to receive a K-wire therethrough and into said bone;

wherein the K-wire barrels extend non-parallel to each other;

iv) a block fastener;

v) a compression block that is detachably attached to the bone plate, wherein said block fastener is configured for insertion through a block fastener aperture through the compression block and into said plate-block threaded aperture, said compression block comprising:

a block screw aperture configured to receive the block end of the jacking screw; wherein the sled end of the jacking screw is coupled with the sled;

vi) a pair of sled guide pins configured on opposing sides of the single jacking screw and configured to extend between the sled assembly and the compression block, wherein each of said sled guide pins is configured to linearly translate within and with respect to the compression block;

vii) a cutting guide coupled with the sled assembly and comprising:

a first guide slot; and second guide slot;

b) attaching the compression block to the bone plate by inserting the block fastener through the block fastener aperture in the compression block and into the plate-block threaded aperture in the bone plate;

c) coupling the sled assembly to the bone plate includes configuring the sled channel over the bone plate and configuring the sled channel extensions below the sled flanges and then sliding the sled assembly to position the sled channel extension under the sled flanges with respect to a top side of the bone plate to retain the sled assembly to the bone plate;

d) coupling the pair of sled guide pins between the sled assembly and the compression block, wherein the single jacking screw extends from the sled assembly to the compression block generally parallel with the length axis of the bone plate;

wherein the single jacking screw extends into the block screw aperture of the compression block;

e) configuring the bone plate over said bone;

f) securing the bone plate to said bone by inserting a first end bone fastener through the first end bone fastening aperture and into said bone;

g) inserting a slotted bone fastener through the slotted fastener aperture and into said bone;

h) inserting K-wires through the pair of K-wire barrels and into the bone;

i) cutting a bone portion for resection using a cutting implement inserted through the first guide slot to produce a first cut in said bone and through the second guide slot to produce a second cut in said bone;

j) resecting the bone portion to produce a first cut bone end on a first cut portion of bone and a second cut bone end on a second cut portion of bone;

k) turning the single jacking screw to move the sled assembly toward the compression block, wherein said K-wires force the second cut end toward the first cut end, and wherein the sled flanges of the bone plate slide within the sled channel while being retained by the sled channel extensions;

l) inserting a spanning bone fastener through the spanning bone fastener aperture;

wherein the spanning bone fastener extends from the second cut portion of bone across the second cut bone end and into the first cut portion of bone across the first cut bone end;

m) securing the second cut portion of bone to the bone plate by inserting a second end bone fastener through said second end fastening aperture and into the second cut portion of bone;

n) removing the K-wires; and o) removing the compression block and the sled assembly.

* * * * *